(12) United States Patent
Borrello

(10) Patent No.: US 8,434,482 B2
(45) Date of Patent: May 7, 2013

(54) CLOSED LOOP CONTROL SYSTEM FOR A HIGH FREQUENCY OSCILLATION VENTILATOR

(75) Inventor: Michael A. Borrello, Carlsbad, CA (US)

(73) Assignee: CareFusion 207, Inc., San Diego, CA (US)

( * ) Notice: Subject to any disclaimer, the term of this patent is extended or adjusted under 35 U.S.C. 154(b) by 127 days.

(21) Appl. No.: 12/952,770

(22) Filed: Nov. 23, 2010

(65) Prior Publication Data

US 2011/0126833 A1 Jun. 2, 2011

Related U.S. Application Data

(62) Division of application No. 11/376,648, filed on Mar. 15, 2006, now Pat. No. 7,861,716.

(51) Int. Cl.
*F16K 31/02* (2006.01)

(52) U.S. Cl.
USPC ............ 128/204.21; 128/204.18; 128/205.18; 128/204.23

(58) Field of Classification Search ............. 128/200.24, 128/204.18, 204.21, 205.18, 204.23, 898; 417/437
See application file for complete search history.

(56) References Cited

U.S. PATENT DOCUMENTS

| | | | |
|---|---|---|---|
| 3,201,529 A | 8/1965 | Surh et al. | |
| 4,409,977 A | 10/1983 | Bisera | |
| 4,495,947 A | 1/1985 | Motycka | |
| 4,617,637 A | 10/1986 | Chu | |
| 4,719,910 A * | 1/1988 | Jensen | 128/204.21 |
| 4,747,402 A | 5/1988 | Reese et al. | |
| 4,788,974 A | 12/1988 | Phuc | |
| 4,805,612 A * | 2/1989 | Jensen | 128/204.21 |
| 4,821,709 A * | 4/1989 | Jensen | 128/204.21 |
| 4,838,259 A | 6/1989 | Gluck | |
| 5,107,830 A | 4/1992 | Younes | |
| 5,237,987 A | 8/1993 | Anderson | |

(Continued)

FOREIGN PATENT DOCUMENTS

| | | |
|---|---|---|
| EP | 0512285 | 11/1992 |
| EP | 956877 | 11/1999 |

(Continued)

OTHER PUBLICATIONS

Simon, B. et al. "Design and Calibration of a High-Frequency Oscillatory Ventilator". (1991) IEEE Transactions on Biomedical Engineering. vol. 38, No. 2. pp. 214-218.*

*Primary Examiner* — Justine Yu
*Assistant Examiner* — Valerie L Skorupa
(74) *Attorney, Agent, or Firm* — McDermott Will & Emery LLP

(57) ABSTRACT

A control system for a high frequency oscillating ventilator (HFOV) includes an oscillator controller and a mean airway pressure (MAP) controller. The HFOV includes a reciprocating piston which is adapted to generate positive and negative pressure waves for delivery to a patient airway. The oscillator controller comprises a pair of closed loop control circuits including an oscillator pressure loop and a centering loop which are collectively adapted to regulate frequency and amplitude of piston reciprocations and centering of the piston. The MAP controller comprises a closed loop control circuit that is adapted for regulating MAP at the patient utilizing feedback in the form of patient circuit pressure. Likewise, the oscillator controller utilizes patient circuit pressure as well as piston displacement feedback in order to regulate movement of the piston.

8 Claims, 2 Drawing Sheets

U.S. PATENT DOCUMENTS

| | | | |
|---|---|---|---|
| 5,307,794 | A | 5/1994 | Rauterkus et al. |
| 5,542,415 | A | 8/1996 | Brody |
| 5,555,880 | A * | 9/1996 | Winter et al. ............ 128/204.21 |
| 5,632,269 | A | 5/1997 | Zdrojkowski |
| 5,692,497 | A | 12/1997 | Schnitzer et al. |
| 5,704,346 | A | 1/1998 | Inoue |
| 5,755,223 | A | 5/1998 | Schaible et al. |
| 6,085,746 | A | 7/2000 | Fox |
| 6,158,433 | A | 12/2000 | Ong et al. |
| 6,371,113 | B1 | 4/2002 | Tobia |
| 6,390,092 | B1 | 5/2002 | Leenhoven |
| 6,557,554 | B1 | 5/2003 | Sugiura |
| 6,581,597 | B2 | 6/2003 | Sugiura |
| 6,591,836 | B1 | 7/2003 | Fuhrman |
| 6,595,213 | B2 | 7/2003 | Bennarsten |
| 6,640,807 | B2 | 11/2003 | Bennarsten |
| 6,694,978 | B1 | 2/2004 | Bennarsten |
| 6,910,485 | B2 | 6/2005 | Faries, Jr. et al. |
| 6,948,497 | B2 | 9/2005 | Zdrojkowski et al. |
| 7,164,336 | B2 | 1/2007 | Rausch et al. |
| 2001/0020473 | A1 * | 9/2001 | Bennarsten ............... 128/204.21 |
| 2002/0157187 | A1 * | 10/2002 | Ozarowski et al. ............... 5/689 |
| 2005/0113703 | A1 | 5/2005 | Farringdon et al. |

FOREIGN PATENT DOCUMENTS

| | | |
|---|---|---|
| EP | 1106197 | 6/2001 |
| JP | 05-115554 | 5/1993 |
| JP | 07-246240 | 9/1995 |
| JP | 10-295099 | 11/1998 |
| JP | 2001-505467 | 4/2001 |
| JP | 2004-500905 | 1/2004 |
| JP | 2004-508105 | 3/2004 |
| JP | 11-513600 | 4/2011 |

* cited by examiner

CLOSED LOOP CONTROL SYSTEM FOR A HIGH FREQUENCY OSCILLATION VENTILATOR

CROSS-REFERENCE TO RELATED APPLICATIONS

This application is a divisional application of U.S. patent application Ser. No. 11/376,648, filed Mar. 15, 2006 now U.S. Pat. No. 7,861,716 entitled "CLOSED LOOP CONTROL SYSTEM FOR A HIGH FREQUENCY OSCILATION VENTILATOR," which is related to U.S. application Ser. No. 11/269,488 entitled "HIGH FREQUENCY OSCILLATING VENTILATOR" filed on Nov. 8, 2005, the entire contents of which is expressly incorporated by reference herein.

BACKGROUND

The present invention relates generally to medical equipment, and more particularly, to a closed loop control system for a high frequency oscillating ventilator (HFOV) for producing positive and negative pressure waves in respiratory air that is supplied to a patient. Advantageously, the control system is specifically adapted to allow for accurate control of the pressure oscillations produced by the HFOV while providing a means for accurate control of mean airway pressure (MAP).

As opposed to conventional ventilators which ventilate only during the inhalation phase and which rely on human physiological response for ventilation during the expiration phase, HFOV's produce an active exhalation which is critical in the respiration of certain types of patients such as in neonates and/or other child or adult patients suffering from certain lung diseases. In some cases, the lungs of the patient may be incapable of providing adequate ventilation or gas exchange, particularly during the exhalation phase. In this regard, HFOV's are specifically developed to provide sufficient gas exchange and full oxygenation of a patient whose respiratory abilities in the exhalation phase are compromised.

In a simplified description of an HFOV patient ventilation system, HFOV's typically deliver a relatively small tidal volume to the patient while simultaneously keeping the lungs and alveoli open at a relatively constant airway pressure. The small tidal volume is delivered to the lungs at a relatively fast rate typically measured in breaths per second or Hertz (Hz) wherein 1 Hz is equal to I breath per second. HFOV's typically operate at respiratory rates that greatly exceed the normal breathing rate of a human. For example, HFOV's may operate at a rate of 5 Hz (i.e., 5 breaths per second) whereas the at-rest breathing rate of an adult human is typically less than 1 Hz.

The positive and negative pressure waves or pressure oscillations that are delivered to the patient are typically generated by a piston disposed within the HFOV. The piston is adapted to rapidly move an elastic diaphragm at the desired frequency. The piston may be driven by a linear motor powered by a square-wave driver which induces rapid reciprocation caused by switching of the polarity of the square-wave driver between positive and negative values. Variations in the polarity voltage or current at the square-wave driver cause proportional increases or decreases in piston amplitude.

Because the piston displacement causes the pressure oscillations, the greater the piston amplitude, the greater the tidal volume delivered to the patient. Certain patients may have high resistance in the airway which, in turn, generates greater resistance against which the piston must act during its reciprocation. Therefore, accurate control of the piston movement (e.g., amplitude) is desirable in order to provide the optimal amount of ventilation to the patient.

Furthermore, because HFOV's must also keep the lungs and alveoli open at a generally constant airway pressure and because different patients have differing levels of airway resistance, it is further desirable that MAP is adjustable. Regulation of the MAP in the patient ventilation system is typically facilitated by means of an exhalation valve disposed adjacent to a patient wye. Ideally, the MAP is adjusted such that the lungs and alveoli are maintained at an open state in order to prevent lung inflate/deflate cycles which may be damaging to alveoli over time and which may lead to further complications.

The prior art includes a wide variety of HFOV's that are directed towards generating pressure pulses in the patient circuit or lung system. For example, U.S. Pat. No. 4,409,977 issued to Bisera et al. and entitled High Frequency Ventilator discloses a high frequency breathing apparatus adapted to deliver high frequency air pulses to a catheter that is energized by pressurized air. The Bisera device includes a flexible bag forming a sealed chamber and a pressure source that provides pressure pulses to the chamber to compress the bag at each pulse and thereby deliver air into a catheter that leads to a patient's lungs.

U.S. Pat. No. 4,719,910 issued to Jensen and entitled Oscillating Ventilator and Method discloses an HFOV having a diaphragmatically sealed piston mounted in a housing and being reciprocative therewithin via circuitry that is operable to alternatingly reverse the polarity of current flow into a motor. The Jensen device is connected to the patient's airway via a tube to deliver a polarized pressure wave within a flow of gas delivered to the patient.

U.S. Pat. No. 4,788,974 issued to Phuc and entitled High Frequency Artificial Respirator discloses a high frequency respirator wherein a patient's circuit thereof is supplied with respiration gas and an oscillation generator imparts high frequency oscillation to the respiration gas. Pressure waves created thereby are delivered to gas flow within the patient's circuit which aids diffusion of gas within the air passages and giving artificial respiration to the patient.

U.S. Pat. No. 5,704,346 issued to Inoue and entitled High Frequency Oscillatory Ventilator discloses a device for transmitting high frequency pressure to a patient via reciprocation of a piston. The Inoue device utilizes a sol} bag for absorbing pressure generated by the piston and which allows for adjusting the amount of gas exchange in the patient without altering piston stroke such that a rotary motor may be used for driving the piston.

U.S. Pat. No. 6,640,807 issued to Bennarsten and entitled High Frequency Oscillation Ventilator discloses an HFOV for alternately supplying and removing a volume of gas to and from a patient. The Bennarsten HFOV includes a flow controller for apportioning the volume of gas supplied by the unit in order to establish a desired inspiration tidal volume for delivery to the patient independent of the oscillator volume.

U.S. Pat. No. 4,617,637 issued to Chu et al. and entitled Servo Control System for a Reciprocating Piston Ventilator discloses a control system for moving a piston of an HFOV utilizing non-linear time domain analysis in a predictive servo control system for controlling reciprocative movement of the piston. The predictive servo control system utilizes flow profiles stored in look-up tables as well as pressure and positional information in order to generate control signals for regulating movement of the piston.

Many of the techniques utilized in controlling the above-mentioned HFOV's employ open loop control systems wherein input signals representative of various operating parameters of the HFOV are fed to a controller in order to achieve the desired ventilation characteristics such as MAP and tidal volume. Unfortunately, due to changes in the operating parameters of the HFOV during ventilation of the patient as well as due to changes in physiological response of the patient, inaccuracies may develop in the patient ventilation system including errors in the MAP and errors in piston movement (amplitude and/or frequency). Such inaccuracies may lead to less-than-optimal efficacy of patient ventilation with the risk of complications developing in the patient.

The prior art includes several attempts to overcome the above-mentioned problems of open loop control systems for HFOV's. For example, the Chu reference appears to disclose a servo control system that employs system feedback in the form of flow rate and pressure measurements in an attempt to control MAP with greater accuracy. However, such feedback is only indirectly utilized to control piston movement. In this regard, the control system disclosed in the Chu reference is understood to be a predictive control system that uses a synthetic empirical approach rather than a systematic control system approach that directly utilizes feedback on critical parameters of patient ventilation (i.e., patient circuit pressure) and HFOV operation (i.e., piston movement).

In this regard, prior art control systems, as understood, fail to address the conflicting control goals of HFOV's. More specifically, many of the prior art HFOV's employ control systems that do not allow for accurate control of pressure oscillations produced by the HFOV nor allow for accurate centering of the reciprocating mechanism (i.e., the piston) such that piston amplitude can be maximized without regard to frequency. Without the benefit of centering controls for the piston, closed loop pressure controls alone will cause the piston to drift toward one of opposite ends of its stroke and ultimately interfere with the ability to maintain oscillations. Furthermore, many of the prior art HFOV's are not understood to provide a means for attenuating or decoupling pressure oscillations from MAP control. Finally, the control systems of the prior art HFOV's are not understood to provide an effective and accurate means for improving the rate of response to changes in the MAP.

BRIEF SUMMARY

The above-described deficiencies associated with prior art control systems as applied to HFOV's are specifically addressed and alleviated by the control system of the present invention wherein separate feedback controllers are utilized to control piston movement and MAP. The controllers combine patient circuit pressure feedback and piston position feedback in regulating motion of the piston as well as enabling accurate piston centering. Furthermore, the controller utilizes the patient pressure feedback to regulate an exhalation valve included in the patient ventilator system to provide accurate control of MAP.

In its broadest sense, the control system includes an oscillator controller and a MAP controller. The oscillator controller comprises a pair of closed loop control circuits including an oscillator pressure loop and a centering loop which collectively regulate frequency and amplitude of piston reciprocations and allow for accurate centering of the piston. The MAP controller comprises a closed loop control circuit for regulating MAP at the patient.

The patient ventilator circuit may include a piston position sensor operative to measure piston position in the HFOV and generate a piston displacement signal for feedback to the centering loop. A pressure sensor may be disposed adjacent to a patient wye in the patient ventilator circuit and is preferably configured to measure patient circuit pressure in order to generate a measured pressure signal for feedback to the MAP regulation loop.

The measured pressure signal is also preferably fed to the oscillator pressure loop. The oscillator pressure loop compares the measured pressure signal (generated by the pressure•sensor at the patient wye) to a desired oscillator pressure signal and generate an oscillator pressure error signal in response thereto. The centering loop compares the piston displacement signal generated by the piston position sensor to null or zero as the desired piston position and generates a displacement error signal in response thereto.

Preferably, the piston displacement signal and the measured pressure signal are each filtered in such a manner that the frequency bands thereof are non-overlapping and non-conflicting. In addition, each of the piston displacement signal and measured pressure signal are compared to piston center and desired pressure, respectively, and this difference is filtered through proportional integral (PI) controllers that are operative to reduce differences towards zero and to limit windup in integral components of the respective PI controllers.

Outputs from the PI controllers of the oscillator pressure loop and the centering loop are then combined in order to generate an oscillator command signal which may be in the form of a current or voltage signal in order to drive a current amplifier for powering the HFOV. The current amplifier may be adapted to generate a square wave signal for reversing polarity of the HFOV such that the piston may reciprocate and generate positive and negative pressure waves at the patient.

The MAP regulation loop regulates MAP at the patient by manipulating the exhalation valve which may vent to ambient via an exhalation port. More specifically, feedback in the form of the patient circuit pressure is utilized by the MAP regulation loop and, after filtering to isolate oscillations induced by the oscillator pressure loop and maximize response in the MAP regulation loop, is compared to a desired MAP signal.

The resulting MAP loop error signal is then filtered through an integral controller to generate an exhalation valve command signal for driving a valve actuator. Ideally, the valve actuator responds to the exhalation valve command signal to regulate the amount of force or change in flow area on the exhalation valve to provide stable and accurate control of MAP at the patient in the face of higher frequency pressure oscillations.

BRIEF DESCRIPTION OF THE DRAWINGS

These and other features and advantages of the various embodiments disclosed herein will be better understood with respect to the following description and drawing, in which like numbers refer to like parts throughout, and in which.

DETAILED DESCRIPTION

Figure 1:
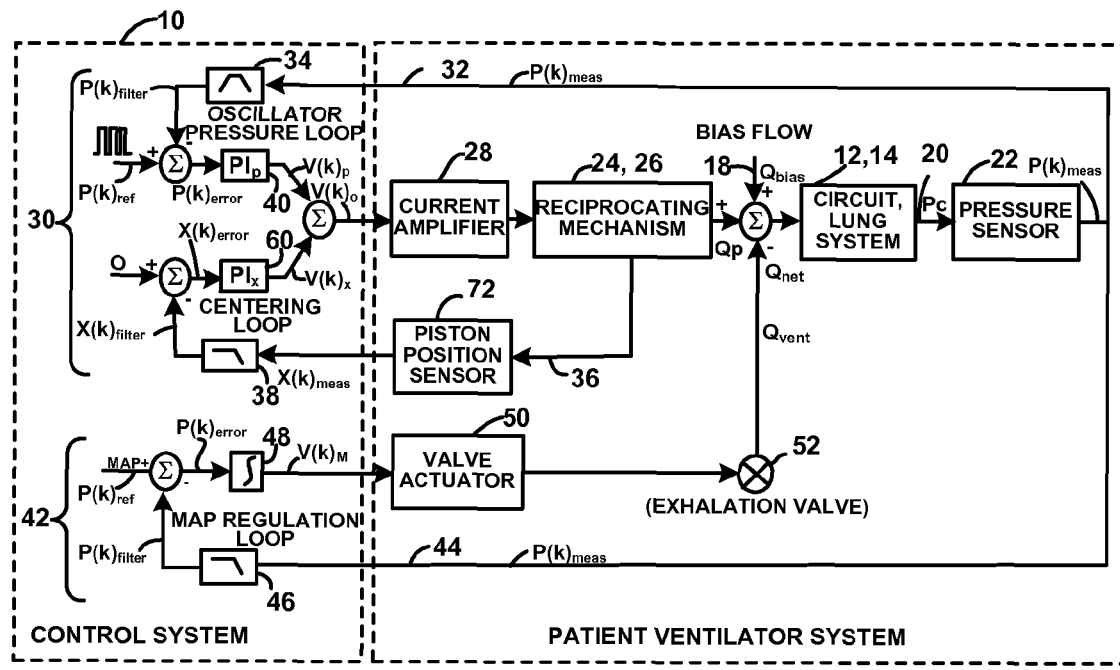
FIG. 1 is a diagram of a closed loop control system for a high frequency oscillating ventilator (HFOV)

Referring now to the drawings wherein the showings are for purposes of illustrating the present invention and not for purposes of limiting the same, shown in FIG. 1 is a closed loop control system 10 for a high frequency oscillating ventilator (HFOV) 26. The control system 10 of the present invention is specifically adapted to provide accurate control of pressure oscillations induced by piston 70 reciprocation within the HFOV 26. Furthermore, the control system 10 of the present invention provides a means for accurate centering of the piston 70 which generates the pressure oscillations.

In addition, the control system 10 of the present invention provides a means for decoupling pressure oscillations from the control of the mean airway pressure (MAP) while maximizing responsiveness of the same. Importantly, the control system 10 achieves the above-noted goals by using feedback of patient circuit pressure Pc and piston 70 position or piston 70 displacement in order to regulate motion of the piston 70 while accurately regulating MAP.

Shown in FIG. 1 is a block diagram of the closed loop control system 10 for an HFOV 26. An exemplary HFOV may be constructed similar to that which is disclosed in U.S. patent application Ser. No. 11/269,488 and entitled HIGH FREQUENCY OSCILLATING VENTILATOR filed on Nov. 8, 2005, the entire contents of which is expressly incorporated by reference herein and having a common assignee with the present application. The HFOV 26 of such type includes a reciprocating mechanism 24 (i.e., piston 70) with the HFOV 26 being connectable to a patient 12 for providing airway pressure thereto.

Figure 2:
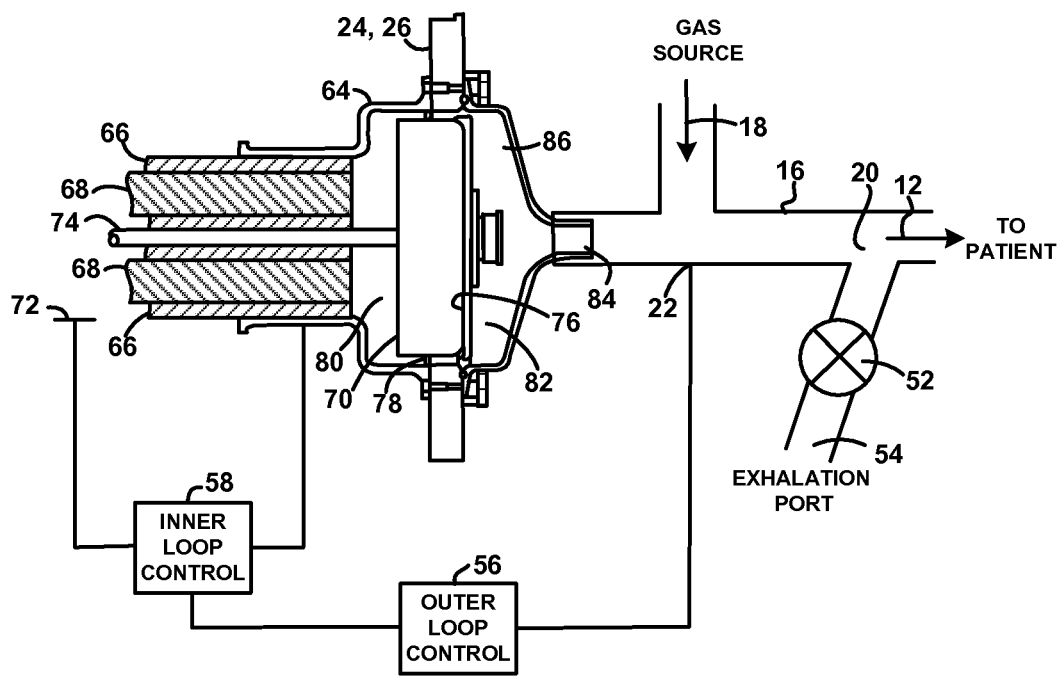
FIG. 2 is a schematic diagram of an HFOV and patient ventilation circuit for which the closed loop control system of the present invention may be incorporated.

FIG. 2 is a schematic diagram of the exemplary HFOV 26 for which the closed loop control system 10 may be adapted for use. As can be seen, the HFOV 26 includes a housing assembly 64 having a linear actuator 66 fixably mounted thereto. A linear coil 68 may be coaxially disposed within the linear actuator 66 and is suspended thereon such as by a pushrod 74 which itself extends axially through the linear actuator 66 in such a manner as to allow reciprocation of the linear coil 68. The piston 70 may be mounted on one end of the pushrod 74 with the linear coil 68 being mounted on an opposite end of the pushrod 74.

Attached to the piston 70 may be a diaphragm 76 which sealingly divides the housing assembly 64 into a first side 80 and a second side 82. The diaphragm 76 may be operatively engaged to the piston 70 and is preferably configured to be removable and/or replaceable such that the HFOV 26 may be transferred between patients. The diaphragm 76 may include a deep radius groove 78 to allow for quiet rolling movement during reciprocation of the piston 70.

Replaceability of the diaphragm 76 may be facilitated through the use of a cone cover 86 removably secured to the housing assembly. Removal of the cone cover 86 allows for access to the diaphragm 76 which may be replaced during patient transfers. An opening 84 formed in the cone cover 86 is connected to the patient 12 by a patient tube 16 which extends to a patient wye 20 shown in FIG. 2. A gas source 18 may be connected to the patient tube 16 and through which oxygen and/or compressed or conditioned air may be delivered in a bias flow Qbias. The patient tube 16 may be connected to the patient airway via an endotracheal tube in order to provide breathing function at the patient airway.

As was earlier mentioned, vibrational energy added to the bias flow Qbias in the form of positive and negative airways produced by the HFOV 26 facilitates the work of breathing by providing positive pressure within the patient airway. Such pressure has been found to enhance both inhalation and exhalation phases wherein carbon dioxide is readily removed from the patient's lungs during the exhalation phase. In this manner, the HFOV 26 promotes the diffusion of oxygen and carbon dioxide to enhance gas exchange. Ideally, the HFOV 26 may be driven by a current amplifier 28 using a square pressure wave profile which has been found to effectuate maximum volume displacement in the patient circuit 14 at a minimum amount of pressure.

As can also be seen in FIG. 2, control of the HFOV 26 is facilitated by inner and outer control loops 58, 56 using a pressure measurement taken at the patient airway and which may be fed to the outer control loop 56. The inner control loop 58 is connected to the outer control loop 56 and receives feedback from a piston position sensor 72 to regulate reciprocative movement of the piston 70 in a manner as will be described in greater detail below.

The patient ventilation circuit may include the exhalation valve 52 fluidly connected to the patient tube 16. The exhalation valve 52 is operative to regulate MAP within the patient circuit/lung system such that the ltmgs are maintained in an approximately inflated condition. Gas is exhaled by the patient 12 to an exhalation port 54 via the exhalation valve 52. As can be seen in FIG. 1, a valve actuator 50 is operative to drive the exhalation valve 52.

As was earlier mentioned, the control system 10 of the present invention utilizes patient circuit pressure Pc and piston 70 position feedback to regulate piston 70 movement within the HFOV 26. In addition, patient circuit pressure Pc feedback is utilized in a separate control loop to regulate the exhalation valve 52 by adjusting pressure forces or flow area there within in order to effectuate the desired MAP. In this manner, the control system 10 provides a means to accurately control the frequency and amplitude of pressure oscillations via control of the piston 70.

Furthermore, the control system 10 provides a means for centering of the piston 70 relative to the HFOV 26 within the bounds of its stroke limits. The control system 10 provides a stable and accurate means for regulating MAP while attenuating input from pressure oscillations caused by piston 70 reciprocation. The control system 10 also provides a means for accurate centering of the piston 70 which thereby allows for maximization of the amplitude of pressure oscillations at any frequency.

Referring in detail now to FIG. 1, the control system 10 of the present invention is comprised of an oscillator controller 30 and a mean airway pressure (MAP) controller 42. The oscillator controller 30 is comprised of a pair of closed loop control circuits which include an oscillator pressure loop 32 and a centering loop 36. Collectively, the oscillator pressure loop 32 and centering loop 36 are adapted to regulate frequency and amplitude of piston 70 reciprocations and centering of the piston 70 by using feedback of the patient circuit pressure Pc and piston 70 position in order to effectuate control of the piston 70. The MAP controller 42 comprises a closed loop control circuit which utilizes patient circuit pressure Pc feedback in order to adjust pressure forces or flow area during venting of the exhalation valve 52 in order to effectively regulate MAP at the patient 12.

The piston position sensor 72 may be configured as an optical sensor, hall sensor, resistive sensor, capacitive sensor, LVDT, or any other suitable displacement or position measurement device for measuring the piston 70 position. The piston position sensor 72 also may generate a piston displacement signal $x(k)_{meas}$ for delivery to the centering loop 36. A pressure sensor 22 such as a pressure transducer may be disposed adjacent to the patient wye 20 and is operative to measure pressure at the patient circuit 14 for feedback to the oscillator controller 30 and MAP controller 42.

The measured pressure signal $P(k)_{meas}$ generated at the patient circuit 14 by the pressure sensor 22 is fed to the oscillator pressure loop 32 which then determines the difference between the measured pressure signal $P(k)_{filter}$ and a desired oscillator pressure $P(k)_{ref}$ signal or command that is provided to the oscillator pressure loop 32. The oscillator pressure loop 32 thereby generates an oscillator pressure error signal $P(k)_{error}$ in response to the difference between the measured pressure signal $P(k)_{meas}$ and the desired oscillator pressure signal $P(k)_{ref}$.

The centering loop 36 is operative to determine the difference between the piston displacement signal $x(k)_{meas}$ generated by the piston position sensor 72 and zero, which represents mid-stroke, as the desired piston 70 position and to generate a displacement error signal $x(k)_{error}$ in response thereto. The oscillator pressure error signal $P(k)_{error}$ and piston displacement error signals $x(k)_{error}$ are then combined to generate an oscillator command signal $V(k)_O$ for regulating reciprocative movement of the piston 70 wherein amplitude and/or frequency of the piston 70 may be regulated.

Importantly, each of the oscillator pressure loop 32 and centering loop 36 includes a band pass filter 34 and a low pass filter 38, respectively, such that the piston displacement signal $x(k)_{meas}$ and the measured pressure signal $P(k)_{meas}$ are filtered to prevent the frequency bands thereof from overlapping and thereby conflicting. As shown in FIG. 1, the centering loop 36 may include a first order low pass filter 38 having a centering loop filter 36 cut off frequency such that the centering loop 36 responds to a limited frequency range of piston 70 displacement Q within the passband of the low pass filter 38. The oscillator pressure loop 32 may in turn include a second order band pass filter 34 having a low cut off frequency that is generally equal to the centering loop low pass filter 38 cut off frequency and a high cut off frequency being such that noise propagation in the oscillator pressure loop 32 is limited. Thus the oscillator pressure loop 32 responds to a limited frequency range of circuit pressure changes within the passband of the band pass filter 34.

The band pass filter 34 may comprise a single pole high pass filter connected in series to a single pole low pass filter. The single pole high pass filter may have a −3 dB cutoff at the −3 dB cutoff frequency of the low pass filter 38 whereas the single pole low pass filter may have a −3 dB cutoff at the high cutoff frequency. The measured pressure signal $P(k)_{meas}$ is filtered by the band pass filter 34 to generate a filtered pressure signal $P(k)_{filter}$, which is then compared to the desired oscillator pressure $P(k)_{ref}$ signal in order to generate the oscillator pressure error signal $P(k)_{error}$. The piston displacement signal $x(k)_{meas}$ is filtered by the low pass filter 38 to generate a filtered displacement signal $x(k)_{filter}$.

Each one of the centering and oscillator pressure loops 36, 32 may further include a oscillator pressure loop proportional integral $PI_P$, controller 40 and a centering loop $PI_x$. Controller 60 which are ideally configured to filter respective ones of the oscillator pressure error signal $P(k)_{error}$ and displacement error signal $x(k)_{error}$ to drive limit these errors toward zero and, furthermore, to limit windup in integral components of the respective $PI_P$ and $PI_x$ controllers 40, 60. Windup in integral components is managed by using known saturation limits of output voltages, the proportional component of the centering loop 36, and a pressure component of the voltage output. Such components are added and/or subtracted from one another in order to establish the integral limits on a step-by-step basis. In this manner, the sum of outputs from each of the $PI_p$ and $PI_x$ controllers 40, 60 are limited to avoid exceeding voltage saturation limits and to keep the oscillator controller 30 attentive when the current amplifier 28 is in saturation.

As was earlier mentioned, the filtered pressure signal $P(k)_{filter}$ is subtracted from the desired oscillator pressure $P(k)_{ref}$ signal in order to determine the error for the oscillator pressure loop 32. The desired oscillator pressure $P(k)_{ref}$ signal is a synthesized periodic signal that may be altered in frequency, amplitude, and/or duty cycle depending on the desired operating parameters of the patient ventilator system as well as upon response by the patient 12. The oscillator pressure error signal $P(k)_{error}$ is filtered by the $PI_p$ controller 40 of the oscillator pressure loop 32 wherein windup in an integral component is limited by using the known saturation limit voltages of the output voltage controls and-the proportional component of the oscillator pressure loop 32. The displacement output signal $V(k)_x$ of the centering loop 36 and the pressure output signal $V(k)_p$ of the oscillator pressure loop 32 are summed to provide the oscillator command signal $V(k)_O$ as a voltage or current control signal for regulating the piston 70 of the HFOV 26.

Using the above-described arrangement, the oscillator controller 30 enables stable and accurate control of the frequency and/or amplitude of the pressure oscillations while providing accurate centering of the piston 70 within its stroke limits such that the size of pressure oscillations may be maximized for any set frequency. In addition, the oscillator controller 30 is configured to provide automatic homing of the piston 70 towards its center position at the start of operation followed by a gradual increase of the oscillations to the desired or specified amplitude in order to avoid saturation in the PI compensators and maintain stability in the control system 10. Toward this end, filters may buffer changes in control settings in order to slowly transition from a previous setting to a new setting. Such changes in settings may apply to frequency, pressure amplitude and/or duty cycle as well as changes in MAP.

Referring still to FIG. 1, the MAP controller 42 comprises the MAP regulation loop 44 which utilizes filtered patient circuit pressure Pc in order to accurately control MAP. Furthermore, the MAP regulation loop 44 provides a means for isolating or attenuating pressure oscillations induced by the oscillator pressure loop for accurate MAP control. The MAP regulation loop 44 regulates the exhalation valve 52 which is in fluid communication with the patient circuit 14 and with the HFOV 26. Tidal volume Qp delivered by the HFOV 26 in combination with bias flow $Q_{bias}$ provided by the gas source 18 is offset by exhalation flow Qvent as controlled by the exhalation valve 52.

The MAP regulation loop 44 preferably includes a low pass filter 46 which is configured to filter the measured pressure signal $P(k)_{meas}$ generated by the pressure sensor 22 in such a manner as to maximize attenuation of oscillations induced by the oscillator pressure loop 32 while maximizing the response of the MAP regulation loop 42. The low pass filter 46 may be configured as any suitable high order, steep cutoff filter such as a six-pole filter having a −3 dB cutoff relative to the desired MAP signal. Alternatively, an eighth order elliptical filter or any other suitable high order, sharp cutoff low pass filter may be used. A filtered pressure signal $P(k)_{filter}$ is compared with a desired MAP signal $P(k)_{ref}$ which may be a preprogrammed signal or a user-input signal. A MAP loop error signal $P(k)_{error}$ is generated in response to the difference between the filtered pressure signal $P(k)_{filter}$ and the desired MAP signal $P(k)_{ref}$.

The MAP loop error signal $P(k)_{error}$ is then filtered by an integral controller 48 that is specifically configured to drive the error towards zero and limit integral action of the MAP loop error signal $P(k)_{error}$ between voltage saturation limits of the exhalation valve actuator 50 or driver. The integral controller 48 generates an exhalation valve command signal $V(k)_m$ which may be a voltage or a current control signal for regulating the force or flow area on the exhalation valve 52 against oscillations as well as against the bias flow $Q_{bias}$ introduced at the patient wye 20. In this manner, the MAP regulation loop 44 provides a stable and accurate means for controlling MAP at the patient.

Also disclosed herein is a method for initializing the centering loop 36 wherein the piston position sensor 72 of an incremental (i.e., relative) type initially senses the position of the piston 70 as it slowly moves under open loop control toward its full stroke forward position. After completing this motion, the piston position sensor 72 measures and records the amount of displacement of the piston 70. Such measurement is compared with a known full stroke of the piston 70 and is used to calculate and correct the piston displacement signal $x(k)_{meas}$ such that it reads zero (0) when the piston 70 is at center. Alternatively, the position sensor 72 may be of an absolute type whereby initial calibration maneuvers may not be needed to determine mid-stroke. By providing the capability for correcting differences between the measured and actual piston displacement, the piston 70 can be more accurately centered which thereby allows for maximization of piston 70 amplitude for any set frequency.

The operation of the control system 10 of the present invention will now be described. Pressure is measured at the patient circuit 14 using a suitable pressure sensor 22 in order to generate the measured pressure signal $P(k)_{meas}$. The measured pressure signal $P(k)_{meas}$ is filtered by band pass filter 34 and is compared to the desired oscillator pressure $P(k)_{ref}$ signal in order to generate the pressure output signal $V(k)_p$ in response thereto. Likewise, piston 70 displacement 36 is measured utilizing the piston position sensor 72 and the piston displacement signal $x(k)_{meas}$ is generated in response thereto. The piston displacement signal $x(k)_{meas}$ is filtered by low pass filter 38 to produce the filtered displacement signal $x(k)_{filter}$ and then subtracted from zero (0) as the desired piston 70 position in order to generate the displacement output signal $V(k)_x$.

The measured pressure signal $P(k)_{meas}$ and piston displacement signal $x(k)_{meas}$ are preferably filtered such that the frequency bands thereof are non-overlapping and non-conflicting and are then passed through the oscillator pressure loop $PI_P$ controller 40 and centering loop $PI_X$ controller 60 and combined to generate an oscillator command signal $V(k)_O$ for regulating piston 70 movement such that the control goals of piston centering and pressure modulation are both met. Preferably, the measured pressure signal $P(k)_{meas}$ is filtered to limit bandwidth thereof from between a predetermined transition frequency and a limiting frequency in order to reduce interaction with the centering loop 36 and to limit loop high frequency noise propagation.

Likewise, the piston displacement signal $x(k)_{meas}$ is filtered to limit bandwidth thereof to between static and the predetermined transition frequency and to reduce interaction with the oscillator pressure loop 32. In this manner, frequency and amplitude of high frequency pressure oscillations may be accurately modulated while providing maximum end-to-end stroke of the piston to allow maximization of pressure oscillations.

As was earlier mentioned, regulation of MAP at the patient 12 is facilitated by using the measured patient circuit pressure Pc feedback in the closed circuit MAP regulation loop 42. The measured pressure signal $P(k)_{meas}$ is filtered and the filtered pressure signal $P(k)_{filter}$ is subtracted from the desired MAP signal $P(k)_{ref}$ in order to generate the MAP pressure error signal $P(k)_{error}$. The MAP pressure error signal $P(k)_{error}$ is then filtered through the integral controller 48 in order to generate the exhalation valve command signal $V(k)_M$ in the form of a current or voltage signal for driving the valve actuator 50. The exhalation valve command signal $V(k)_M$ is proportional to the amount of force or flow area required by the exhalation valve 52 in combination with the bias flow $Q_{bias}$ in maintaining the desired MAP upon which pressure oscillations are superimposed. Furthermore, the selection of the cutoff frequency in low pass filter 46 allows for isolation of the MAP regulation loop 42 from pressure oscillations controlled by the oscillator pressure loop 32 and thereby avoids conflicting response between the loops.

Additional modifications and improvements of the present invention may also be apparent to those with ordinary skill in the art. Thus, the particular combination of parts described and illustrated herein is intended to represent only certain embodiments of the present invention and is not intended to serve as limitations of alternative devices or methods within the spirit and scope of the present invention.

What is claimed is:

1. A closed loop method of regulating piston movement of a piston and mean airway pressure (MAP) in a patient ventilator system having an exhalation valve, the method comprising the steps of:
    measuring a pressure at the patient and generating a measured pressure signal in response thereto;
    comparing a desired oscillator pressure signal to the measured pressure signal and generating a pressure output signal in response thereto;
    measuring piston displacement with respect to a midpoint of full stroke of said piston and generating a piston displacement signal in response thereto;
    subtracting the piston displacement signal from zero as a desired piston position and generating a displacement output signal in response thereto;
    combining the pressure output signal with the displacement output signal and generating an oscillator command signal in response thereto for regulating the piston movement;
    comparing a desired MAP signal to the measured pressure and generating an exhalation valve command signal in response thereto for regulating MAP at the patient; and
    centering said piston about said midpoint of full stroke of said piston while regulating MAP.

2. The method of claim 1 further comprising the step of filtering the measured pressure signal and the displacement output signal such that the frequency bands thereof are non-overlapping.

3. A method of regulating movement of an oscillator piston of a patient ventilator using an oscillator controller comprising an oscillator pressure loop and a centering loop, the method comprising the steps of:
    in the oscillator pressure loop:
    measuring a pressure at the patient and generating a measured pressure signal representative thereof;
    filtering the measured pressure signal to limit bandwidth thereof to between a predetermined transition frequency and a noise-limiting frequency and generating a filtered pressure signal in response thereto;
    receiving a desired oscillator pressure signal;
    summing the filtered pressure signal and the desired oscillator pressure signal and generating an oscillator pressure error signal in response thereto; and
    filtering the oscillator pressure error signal through an oscillator pressure loop proportional integral ($PI_P$) controller and generating a pressure output signal in response thereto; and
    in the centering loop:
    measuring a piston position with respect to a midpoint of full stroke of said piston and generating a piston displacement signal representative thereof;

filtering the piston displacement signal to limit bandwidth thereof to between static and the predetermined transition frequency and generating a filtered displacement signal in response thereto;

subtracting the filtered displacement signal from zero as a desired piston position and generating a displacement error signal in response thereto;

filtering the displacement error signal through a centering loop proportional integral ($PI_X$) controller and generating a displacement output signal in response thereto;

summing the pressure and displacement output signals and generating the oscillator command signal in response thereto for driving the piston movement; and centering said piston about said midpoint of full stroke of said piston while regulating MAP.

4. The method of claim 3 wherein the measured piston displacement signal is filtered using a first order low pass filter with −3 dB rolloff at the transition frequency.

5. The method of claim 3 wherein the measured pressure signal is filtered using a second order band pass filter having a low cutoff frequency generally equal to the centering loop low pass filter cutoff frequency, the band pass filter having a high cutoff frequency being such that noise propagation in the oscillator pressure loop is limited.

6. The method of claim 3 further comprising the steps of:

inducing a change in at least one of frequency, amplitude, and duty cycle settings of the desired oscillator pressure signal;

filtering the change in the settings of the desired oscillator pressure signal in such a manner as to slow the rate of change from a previous setting.

7. The method of claim 3 wherein the patient ventilator includes an exhalation valve for regulating MAP thereat using a MAP regulation loop, the method further comprising the steps of:

receiving the measured pressure signal at the MAP regulation loop;

filtering the measured pressure signal in such a manner as to maximize attenuation of oscillations induced by the oscillator pressure loop and maximize the response of the MAP regulation loop and generating a filtered pressure signal in response thereto;

receiving a desired MAP signal at the MAP regulation loop;

subtracting the filtered pressure signal from the desired MAP signal and generating an MAP pressure error signal in response thereto;

filtering the MAP pressure error signal through an integral controller and generating an exhalation valve command signal in response thereto for driving the exhalation valve.

8. The method of claim 7 wherein the measured pressure signal is filtered using a high order low pass filter with a steep cutoff frequency.

* * * * *